(12) United States Patent
Lutz et al.

(10) Patent No.: US 7,615,282 B2
(45) Date of Patent: *Nov. 10, 2009

(54) EXPANDED PTFE ARTICLES AND METHOD OF MAKING SAME

(75) Inventors: David Isaac Lutz, Newark, DE (US); Norman Ernest Clough, Landenberg, PA (US)

(73) Assignee: Gore Enterprise Holdings, Inc., Newark, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/263,881

(22) Filed: Nov. 3, 2008

(65) Prior Publication Data

US 2009/0061157 A1    Mar. 5, 2009

Related U.S. Application Data

(60) Continuation of application No. 11/865,260, filed on Oct. 1, 2007, now Pat. No. 7,445,843, which is a division of application No. 11/000,414, filed on Nov. 29, 2004, now abandoned.

(60) Provisional application No. 60/605,127, filed on Aug. 26, 2004.

(51) Int. Cl.
    *B32B 27/36* (2006.01)
(52) U.S. Cl. .................. 428/400; 428/364; 428/221; 428/34.1; 428/357; 57/200
(58) Field of Classification Search ............. 428/400, 428/364, 357, 421, 422, 221, 34.1; 57/200
See application file for complete search history.

(56) References Cited

U.S. PATENT DOCUMENTS 3,953,566 A    4/1976    Gore
4,187,390 A    2/1980    Gore
4,208,745 A    6/1980    Okita
4,550,447 A *  11/1985   Seiler et al. ............. 623/1.32
4,647,416 A *  3/1987    Seiler et al. ............. 264/118
5,296,292 A    3/1994    Butters
5,462,781 A *  10/1995   Zukowski ............... 428/36.1
5,466,509 A    11/1995   Kowligi et al.
5,518,012 A    5/1996    Dolan et al.
5,747,128 A    5/1998    Campbell et al.
6,016,848 A    1/2000    Egres, Jr.
6,143,675 A    11/2000   McCollam et al.
6,573,311 B1   6/2003    Martakos et al.
7,060,354 B2   6/2006    Baillie et al.

(Continued)

FOREIGN PATENT DOCUMENTS

WO    WO 95/34252    12/1995

(Continued)

OTHER PUBLICATIONS

International Search Report for PCT/US2005/027878.

*Primary Examiner*—N. Edwards
(74) *Attorney, Agent, or Firm*—Carol A. Lewis White

(57) ABSTRACT

Unique PTFE structures comprising islands of PTFE attached to an underlying expanded polytetrafluoroethylene (ePTFE) structure and to methods of making such structures is disclosed. The ePTFE material may or may not have been exposed to amorphous locking temperatures. These unique structures exhibit islands of PTFE attached to and raised above the expanded PTFE structures.

13 Claims, 11 Drawing Sheets

200X

U.S. PATENT DOCUMENTS

| | | |
|---|---|---|
| 7,179,525 B2 | 2/2007 | Dove |
| 7,445,843 B2 * | 11/2008 | Lutz et al. .................. 428/364 |
| 2005/0086850 A1 * | 4/2005 | Clough ...................... 43/44.98 |
| 2007/0204877 A1 * | 9/2007 | Dolan et al. ................ 132/321 |
| 2008/0034641 A1 * | 2/2008 | Lutz et al. .................. 43/44.98 |

FOREIGN PATENT DOCUMENTS

| | | |
|---|---|---|
| WO | WO 98/01082 | 1/1998 |

* cited by examiner

500X

500X

500X

500X

200X

500X 500X non-plate

500X 500X non-plate 1000X side B

500X

1000X

200X

500X

1000X

Legend:
(1) Example 3
(2) Example 3 island
(3) Example 3 core
(4) Precursor
(5) Comparative 3A
(6) Comparative 3B

100X

100X

1000X 200X  　　　200X

500X

500X

2000X

2000X

2000X

2000X

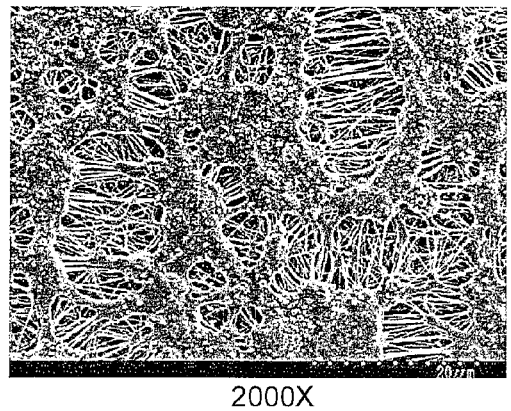
FIG. 31
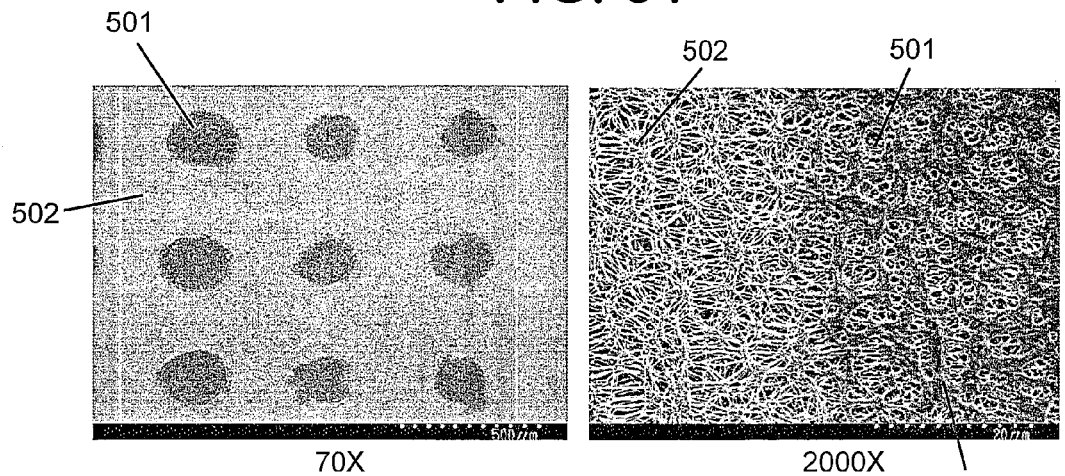
FIG. 32  FIG. 33
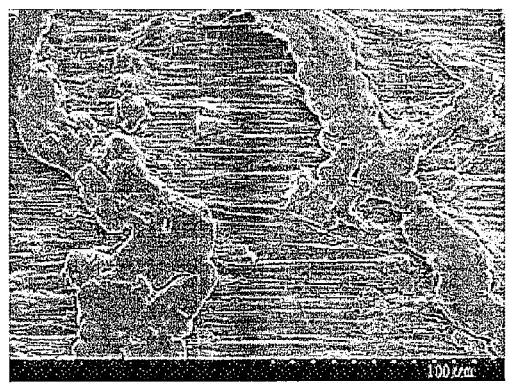
FIG. 34

EXPANDED PTFE ARTICLES AND METHOD OF MAKING SAME

RELATED APPLICATIONS

The present application is a continuation of U.S. patent application Ser. No. 11/865,260, filed Oct. 1, 2007, now U.S. Pat. No. 7,445,843, which is a divisional of U.S. patent application Ser. No. 11/000,414 filed Nov. 29, 2004, now abandoned, which was based on U.S. Provisional Patent Application 60/605,127 filed Aug. 26, 2004, now abandoned.

FIELD OF THE INVENTION

The present invention relates to unique expanded PTFE articles. More specifically, it is directed to novel structures of expanded PTFE and a novel process for preparing the structures.

BACKGROUND OF THE INVENTION

The structure of expanded PTFE ("ePTFE") is well known to be characterized by nodes interconnected by fibrils, as taught in U.S. Pat. Nos. 3,953,566 and 4,187,390, to Gore, and which patents have been the foundation for a significant body of work directed to ePTFE materials. The node and fibril character of the ePTFE structure has been modified in many ways since it was first described in these patents. For example, highly expanded materials, as in the case of high strength fibers, can exhibit exceedingly long fibrils and relatively small nodes. Other process conditions can yield articles, for example, with nodes that extend through the thickness of the article.

Surface treatment of ePTFE structure has also been carried out by a variety of techniques in order to modify the ePTFE structure. Okita (U.S. Pat. No. 4,2308,745) teaches exposing the outer surface of an ePTFE tube, specifically a vascular prosthesis, to a more severe (i.e., higher) thermal treatment than the inner surface in order to effect a finer structure on the inside than on the outside of the tube. One of ordinary skill in the art will recognize that Okita's process is consistent with prior art amorphous locking processes, the only difference being preferential exposure of the outer surface of the ePTFE structure to greater thermal energy.

Zukowski (U.S. Pat. No. 5,462,781) teaches employing plasma treatment to effect removal of fibrils from the surface of porous ePTFE in order to achieve a structure with freestanding nodes on the surface which are not interconnected by fibrils. No further treatment after the plasma treatment is disclosed or contemplated in the teachings.

Martakos et al. (U.S. Pat. No. 6,573,311) teach plasma glow discharge treatment, which includes plasma etching, of polymer articles at various stages during the polymer resin processing. Martakos et al. distinguish over conventional processes by noting that the prior art techniques operate on finished, fabricated and/or finally processed materials, which are "ineffective at modifying bulk substrate properties, such as porosity and permeability." Martakos et al. teach plasma treating at six possible polymer resin process steps; however, no such treatment with or subsequent to amorphous locking is described or suggested. Again, the focus of Martakos et al. is to affect bulk properties such as porosity and/or chemistry quality in the finished articles.

Other means of creating new surfaces on porous PTFE and treating the surface of porous PTFE abound in the prior art. Butters (U.S. Pat. No. 5,296,292) teaches a fishing flyline consisting of a core with a porous PTFE cover that can be modified to improve abrasion resistance. Abrasion resistance of the flyline is improved by modifying the outer cover either through adding a coating of abrasion resistant material to it or by densifying the porous PTFE cover.

In a further example, Campbell et al (U.S. Pat. No. 5,747,128) teach a means of creating regions of high and low bulk density throughout a porous PTFE article. Additionally, Kowligi et al. (U.S. Pat. No. 5,466,509) teach impressing a pattern onto an ePTFE surface, and Seiler et al. (U.S. Pat. No. 4,647,416) teach the scoring PTFE tubes during fabrication in order to create external ribs.

However, none of the prior art references teach applicants' unique combination of processing to create a unique surface on PTFE which has heretofore not been seen.

SUMMARY OF THE INVENTION

The present invention is directed to a unique PTFE structure comprising islands of PTFE attached to an underlying expanded polytetrafluoroethylene (ePTFE) structure and to methods of making such a structure. The ePTFE material may or may not have been exposed to amorphous locking temperatures. These unique structures exhibit islands of PTFE attached to and raised above the expanded PTFE structures. By "raised" is meant that when the article is viewed in cross-section, such as in a photomicrograph of the article cross-section, the islands are seen to rise above the baseline defined by the outer surface of the underlying node-fibril structure by a length, "h." Referring to FIG. 1, which shows a cross-section of an expanded PTFE fiber 10 with island 12, the height of the island 12 rises a height "h" above the surface 14, or "baseline," of the underlying ePTFE structure.

These raised regions, or islands, are connected at their bases to the underlying ePTFE structure. The islands are distinguishable from the underlying nodes and fibrils because of their much larger size. The largest length dimension of the islands is at least twice that of the same dimension of the underlying nodes. This length difference can even exceed 100 times that of the underlying nodes. Further, the morphology of the islands tends to distinguish them from the underlying ePTFE structure. This island structure is unique to the surface of the article and is not present below the surface.

The morphology of the PTFE structures of the present invention may also vary widely with respect to the number of islands present on a given surface area. In many cases, the islands are large and not interconnected. In other embodiments, the islands are interconnected and may appear as a porous covering or web atop the ePTFE structure. Given the expanse of the web, its size greatly exceeds that of underlying nodes.

The unique character of the present articles and processes enable the formation of improved products not seen to date. For example, PTFE fibers can be made according to invention having improved performance in such areas as dental floss, fishing line, sutures, and the like. PTFE articles in membrane, tube, sheet and other forms can also provide unique characteristics in finished products. These and other unique features of the present invention will be described in more detail herein.

DETAILED DESCRIPTION OF FIGURES

The operation of the present invention should become apparent from the following description when considered in conjunction with the accompanying drawings, in which:

FIG. 31 is a photomicrograph of the inventive material made in accordance with Example 8.

FIGS. 32 and 33 are photomicrographs of the inventive material made in accordance with Example 9.

FIG. 34 is a photomicrograph of the inventive material made in accordance with Example 10.

DETAILED DESCRIPTION OF THE INVENTION

Figure 1:
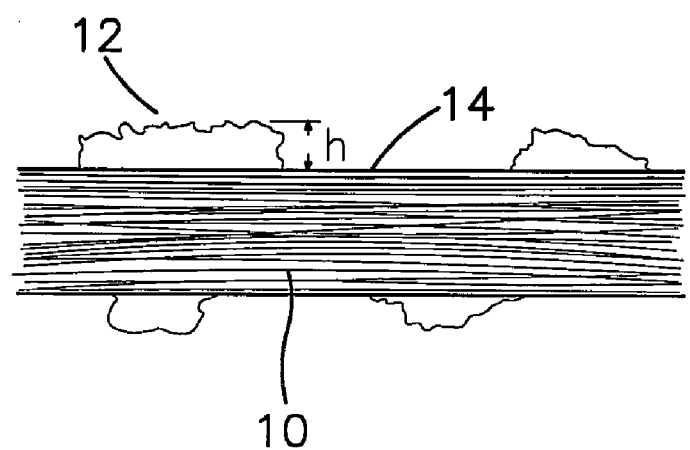
FIG. 1 is perspective view of a cross-section of a fiber in accordance with the present invention showing islands of PTFE above the surface of the underlying ePTFE structure.

The PTFE articles of the present invention comprise islands of PTFE attached to an underlying ePTFE structure. No prior art material exhibits these unique structures of PTFE islands attached to underlying ePTFE material. The identity of the island material can be confirmed by a variety of techniques. For instance, the island material can be assessed by scraping bits of just the island material off the surface with a razor blade, or by other suitable means, then performing a thermal analysis on the sample. Differential Scanning Calorimetry (DSC) analysis of the islands, described later herein, indicates the absence of a node and fibril structure.

Articles of the present invention are also unique in that the islands of PTFE are of lower molecular weight than the PTFE of the underlying ePTFE structure. This difference in molecular weight can be inferred from measuring and comparing the exotherms of the cooling curves obtained from differential scanning calorimetry. Furthermore, the heating curves indicate that the underlying ePTFE material possesses melt temperatures at or about 327° C. and 380° C. The raised islands do not exhibit the melt temperature at or about 380° C.

The fundamental process for practicing the present invention is to first subject precursor ePTFE articles to a high-energy surface treatment followed by a heating step to achieve the unique PTFE islands on the surface of the underlying ePTFE material. Solely for convenience the term "plasma treatment" will be used to refer to any high-energy surface treatment, such as but not limited to glow discharge plasma, corona, ion beam, and the like. It should be recognized that treatment times, temperatures and other processing conditions may be varied to achieve a range of island sizes and appearances. For example, the PTFE surface can be plasma etched in an argon gas or other suitable environment, followed by a heat treating step. Neither heat treating the ePTFE alone nor plasma treating alone without subsequent heat treating results in articles of the present invention.

This inventive process can be applied to a vast array of types and shapes of articles including, but not limited to, tubes, fibers, including but not limited to twisted, round, flat and towed fibers, membranes, tapes, sheets, rods, and the like, each possessing any of a variety of cross-sectional shapes. Depending on the morphology of the precursor ePTFE material, the appearance of the islands can vary significantly, and the process produces a more dramatic effect in certain precursor materials. For example, larger islands appear to be produced in precursor materials possessing long fibrils and small nodes when processed in accordance with the teachings of the present invention.

In a further embodiment, the present invention also includes the step of filling just the surface of ePTFE with other materials. Filler particles can be applied to the surface of the ePTFE article after the plasma treatment step, before the heat treatment step. This process is referred to as surface filling, as distinguished from conventional means of filling the pores of porous ePTFE articles, which may include such techniques as blending or co-coagulation of the filler material with PTFE, impregnating the pores with filler, and altering the surface then bonding other materials to that surface. The particles were primarily contained within the islands as opposed to lying on the surface, as they were prior to the heat treating step.

Articles of the present invention possess surprising and valuable features heretofore unobtainable. In one embodiment, dental floss materials consisting essentially of PTFE are found to have significantly increased grippabililty and abrasive characteristics. Grippability refers to the ability to firmly grip the floss during use such that it does not slide between the user's fingers. The abrasiveness provides the user with an improved cleaning sensation, if not with improved cleaning, as well. These characteristics have not been realized to this degree in conventional PTFE floss materials.

The abrasiveness feature affords the creation of articles consisting essentially of PTFE that possess all of the advantages of PTFE and ePTFE, without being lubricious. Lubricity is not a desirable feature in all applications.

Surprisingly, articles of the invention can simultaneously exhibit increased abrasiveness evidenced by an increased drag coefficient and improved abrasion resistance, as evidenced by improved durability in abrasion tests. Durability tests described herein quantify the fray resistance of articles. Even though the precursor material is subjected to a plasma treatment step that would otherwise be expected by one of skill in the art to compromise the abrasion resistance of the article, by virtue of the subsequent heat treating step, the inventive article is surprisingly more abrasion resistant than the precursor article. This degree of abrasion resistance had heretofore only been achieved with ePTFE floss materials with bulk densities less than about 0.8 g/cc.

The abrasion resistance also is particularly useful in solving fraying problems associated with ePTFE fibers, especially with ePTFE fishing lines.

The islands of PTFE have also been demonstrated to improve the knot holding strength of suture materials made in accordance with the inventive process.

The presence of the islands may also enhance bonding inventive articles to other articles, especially perfluoropolymer articles, PTFE articles in particular.

The present invention will be further described with respect to the non-limiting Examples provided below.

Test Methods

Drag Resistance Test

Figure 2:
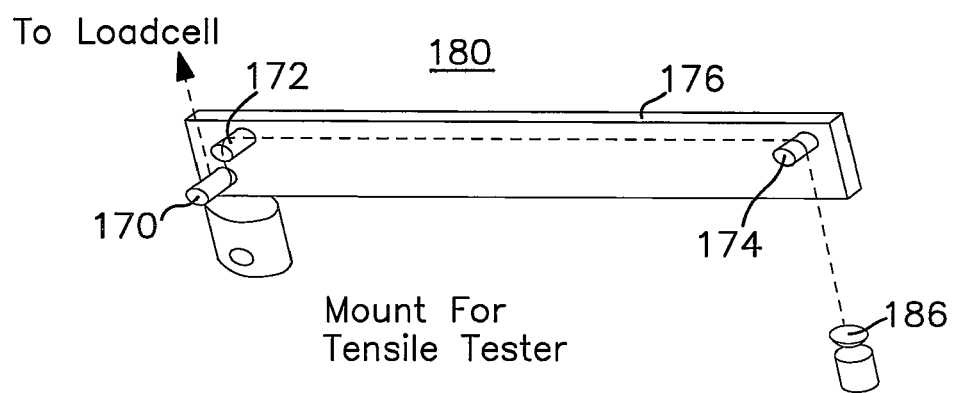
FIG. 2 is perspective view of a fixture set-up for measuring mechanical properties of materials of the present invention as described in more detail herein.

Dynamic drag resistance was determined using a fixture 180 as shown in FIG. 2 using three 12.7 mm (0.50 inch) diameter cylindrical shafts mounted on a rigid beam which was cantilevered from a standard tensile tester, Model 5567 from INSTRON Company (Canton, Mass.). The fixture arm support 176 was drilled and reamed nominal 12.7 mm diameter (nominal 0.500 inch diameter) for a running fit of three cylinders 170, 172 and 174 (available from McMaster-Carr Supply Company, Dayton, N.J., Part Number 8524-K24, off-white, G-7 Garolite Glass Silicon Rod material nominal 12.7 mm diameter, and parted off at nominal lengths of 25 mm) in the fixture arm support, which were secured using set-screws compressing radially on the cylinders at the cylinder-support interface. The cylinders were secured such that they did not rotate during a test iteration and extended out of the test fixture approximately 17 mm. All three cylinders were parallel which each other and perpendicular with the cantilever fixture arm support 176.

The surface roughness ($R_a$) of the three cylinders was measured both axially and radially using a Perthometer Model M4P (Feinpruef Perthen, GmbH, Posffach 1853, D-3400 Goettingen, Germany). $R_a$ was measured in the cylinder axial direction at 4 quadrants 90 degrees apart measured using a stroke 0.03 inch. For the $R_a$ in the cylinder radial direction, 3 to 4 measurements were taken using a 0.01 inch stroke randomly along the length of the cylinder. The results are presented in the table below.

| Cylinder Number | $R_a$ Measurements - Axial (microinches) | $R_a$ Measurements - Radial (microinches) |
| --- | --- | --- |
| 1 | 93/122/102/103 | 55/56/59 |
| 2 | 32/27/67/55 | 101/53/48/69 |
| 3 | 52/57/118/66 | 60/98/68/40 |
| Average $R_a$: | 74.5 | 64.3 |
| Standard Deviation: | 32.3 | 19.2 |

Before each sample was tested, the cylinders were removed from the fixture, completely submerged in a beaker containing 99.9% isopropanol alcohol for 1 minute, replaced in the test fixture and permitted to air dry completely.

The INSTRON 5567 tensile tester was outfitted with a one yarn style clamping jaw suitable for securing filament samples during the measurement in the mode of tensile loading. The jaw was connected to a 100 Newton rated load cell (not shown) which was secured on the tester's cross-head. The cross-head speed of the tensile tester was 30.48 cm per minute, and the gauge length was 50 mm (measured from the tangent point of the yarn clamp down to the tangent point of the test specimen resting against the first of the three cylinders 170). The fixture 176 was secured to the tensile tester such that the test specimen secured in the clamping jaw was perpendicular to the axis of cylinder 170.

The test article was threaded around the three cylinders 170, 172 and 174 in the manner depicted in FIG. 2. Consequently, the sample was wrapped halfway around cylinder 170 and a quarter of the way around cylinders 172 and 174. Hence, a total cumulative wrap angle of one full wrap (i.e., $2\pi$ radians) was achieved.

The vertical distance between the center points of cylinders 170 and 172 tangent points was 25.4 mm. The horizontal distance between the center points of the same two cylinders was 12.7 mm. The horizontal distance between the center points of cylinders 172 and 174 was 360.4 mm.

Since the inventive material may be produced to provide islands on only one side of the material, the samples were all twisted so that the same side contacted the surface of all three cylinders. This results in placing a one turn twist in all test specimens between cylinders 170 and 172. The test specimens had no twist between cylinders 172 and 174. A 300 gram weight 186 was fixed to the end of the test specimen. The length of the test specimen extending past cylinder 174 and down to the suspended 300 gram weight 186 was at least 110 mm, but no more than 510 mm.

In order to determine drag resistance of samples, five samples long enough to conduct the test were randomly selected and tested. To begin the test, the tensile tester cross-head was set to move upwards, thus causing the 300 gram weight to move upwards as well. The test specimen slid over the three cylinders for at least a travel length of 80 mm, but no more than 510 mm. The load cell was connected to a data acquisition system such that the load induced as the test specimen slid over the cylinders during the upward motion of the cross-head was recorded at a rate of at least 10 data points per second. The data acquisition system recorded the corresponding cross-head displacement during the testing as well. The drag resistance at each cross-head displacement was then calculated by the following formula:

$$e^{(\delta\theta)} = T_2/T_1, \text{ which reduces to: } \delta = [\ln(T_2/T_1)]/\theta,$$

where:
$\delta$ = Drag Resistance
$\theta$ = Cumulative Wrap Angle in Radians = $2\pi$ radians
$T_1$ = average input tension = 300 grams
$T_2$ = average output tension as recorded by data acquisition in gram force
(Note: ln is the Natural Logarithm Base on e=2.71828)

Data were obtained for displacements between 0 mm to 76 mm. The dynamic drag resistance was determined by using the arithmetic mean-calculated drag resistance over the displacement between 25.4 and 50.8 mm.

Note that samples possessing a wax or other coating can be tested after removing the coating material. Wax coating, for example, can be removed by soaking the floss in a heated bath at 60 deg C. of reagent grade isopropanol alcohol for 10 minutes and then wiping the wax away using a soft cotton cloth.

Knot Holding Capacity Test for Sutures

Samples were prepared in the following manner: A length of the sample suture material was wrapped twice around a 2-inch diameter smooth surfaced (for example, Delrin) cylinder. The ends were tied together using 4 sliding throws, and one alternate-sliding throw to lock. Throws were tensioned so that the knot was positioned against the cylinder. The "ears" (ears are the two free ends of the suture after the knot is tied) were trimmed to lengths between 1/8 and 3/16-inch. The sample was slipped off of the cylinder and the loop was cut in half at a location opposite the knot.

Samples were tested using an INSTRON Model 5500R testing machine at a 200 mm/min cross-head speed and 229 mm gauge length. Yarn grips and a 10-kg load cell were used. At least ten samples were tested and the peak force results were averaged (regardless of whether peak force occurred by breaking or slippage of the knot). All samples were tested in the temperature range of 22-24° C.

Island Height Measurement

Island height was measured from scanning electron micrographs of longitudinal cross-sections of the samples. Individual values of island height were measured as the shortest distance from the node-fibril ePTFE structure to the highest point of the overlying island. A line was drawn across the top surface of the node-fibril structure adjacent to the island. A perpendicular line was then dropped from the highest point on the island to the line on the surface of the node-fibril structure.

The length of the dropped line is the island height. Measurements were preferably taken from micrographs taken at sufficiently high magnification to enable a clear determination of the height, taking into account the magnification of the scale bar at the bottom corner of the figure. Individual measurements were taken for five randomly chosen islands that were representative of all the islands. The reported island height value is the average of those five individual measurements.

Test Method for Determination of Crystalline Phases in Polytetrafluoroethylene Material Based on Differential Scanning Calorimetry Differential Scanning Calorimetry (DSC) can be used to identify the crystalline phases of polytetrafluoroethylene (PTFE). The presence of endothermic peaks during a heating scan, at approximately 320-340° C. shows the typical melting phases of PTFE. In addition, an endotherm at approximately 380° C. is a consequence of PTFE having been expanded, thereby creating a node-fibril structure. This peak (or endotherm) is widely recognized to be indicative of the presence of fibrils in the test sample.

This test was performed using a TA Instruments Q1000 DSC and TA Instruments standard aluminum pans and lids for Differential Scanning Calorimetry (DSC). A TA Instruments Sample Encapsulation Press (Part No. 900680-902) was used to crimp the lid to the pan. Weight measurements were performed on a Sartorius MC 210P microbalance.

Calibration of the Q1000 was by performed by utilizing the Calibration Wizard available through the Thermal Advantage software supplied with the device. All calibration and resulting scans were performed under a constant helium flow of 25 ml/min.

Samples were prepared by either cutting pieces (6 mm or smaller) of fiber or by loading already prepared surface and core material using a scraping method (described elsewhere herein). One pan and lid were weighed on the balance to 0.01 mg precision. The sample material was loaded into the pan and also recorded to 0.01 mg precision, with samples ranging from slightly under 1.0 mg for surface scraping samples to nearly 3.0 mg for some fiber samples. These values were entered info the Thermal Advantage control software for the Q1000. The lid was placed on the pan and was crimped using the press. Care was taken to ensure that no sample material was caught in the crimp between the lid and the pan. A similar pan for reference was prepared, with the exception of the sample article, and its weight was also entered into the software. The pan containing the sample article was loaded onto the sample sensor in the Q1000 and the empty pan was loaded onto the reference sensor. The samples were then subjected to the following procedure:

1: Equilibrate at −30.00° C.
2: Ramp 10.00° C./min to 400.00° C.
3: Mark end of cycle 0
4: Isothermal for 5.00 min
5: Mark end of cycle 0
6: Ramp 10.00° C./min to 200.00° C.
7: End of method Data were analyzed, unaltered, using Universal Analysis 2000 v.4.0C from TA Instruments. Where data were being analyzed qualitatively (for the presence and temperature location of peaks), scans run under T4P mode were used. In the case of quantitative interpretation of crystallization peaks (specifically, for the measurement of enthalpy), scans were run under T1 mode.

Tensile Break Load and Matrix Tensile Strength (MTS) for Membrane Examples

Tensile break load was measured using an INSTRON 5567 tensile test machine equipped with flat-faced grips and a 10 kN load cell. The gauge length was 2.54 cm and the cross-head speed was 25.4 cm/min. The sample dimensions were 6.35 cm×0.635 cm. For longitudinal MTS measurements, the larger dimension of the sample was oriented in the machine (also known as the down web) direction. For the transverse MTS measurements, the larger dimension of the sample was oriented perpendicular to the machine direction, also known as the cross web direction. Each sample was weighed using an A&D scale, (Milpitas, Calif.), Model #FR-300, then the thickness of the samples was taken using the Heidenhain thickness gauge Model # MT-60M (Schaumburg, Ill.). The samples were then tested individually on the tensile tester. Five different sections of each sample were measured. The average of the five break load (i.e., the peak force) measurements was used. The longitudinal and transverse MTS were calculated using the following equation:

$$MTS=(\text{break load/cross-section area})*(\text{density of PTFE})/\text{bulk density of the porous article}),$$

wherein the density of PTFE is taken to be 2.2 g/cc.

MTS Calculation and Tenacity Measurement for Fiber and Suture Examples

For fiber materials, matrix tensile strength was derived from tenacity values. Tenacity was calculated using break load and sample weight data. Prior to tensile testing, the fiber denier was determined by weighing a 9 m length sample of the fiber using an analytical balance (model AA160, Denver Instruments. Inc., Göttingen, Germany). The mass of the fiber expressed in grams was multiplied by 1000 to arrive at the denier value. The 9 m long fiber sample was cut into five lengths for subsequent break load testing. Tensile testing was conducted at ambient temperature on an INSTRON 5567 tensile test machine equipped with fiber grips and a 10 kN load cell, set to a sample length of 269 mm. The sample was loaded into the grips and clamped. The break load was recorded as the grips move apart at a speed of 254 mm/min. The tenacity of each fiber sample (expressed in grams/denier) was calculated by dividing the break load (expressed in grams) by the denier value of the fiber. The tenacity values for five samples were calculated and then averaged. Matrix tensile strength was then calculated by multiplying the tenacity value (in grams/denier) by 26,019.

Density Measurement

Fiber density was determined using one of two techniques. For fiber densities greater than 1, the "principle of buoyancy," or Archimedes principle, was used, which states that a body immersed in a fluid will be subjected to a buoyancy force equal to the weight of the displaced fluid. Buoyancy force, or the weight of the displaced fluid, is calculated from the initial fiber sample mass and the fiber sample mass during full immersion in the fluid. From the mass of the displaced fluid and the fluid density, the fluid volume displaced can be calculated and represents the total volume of the fiber. Using the initial "dry" mass of the fiber and the fiber volume, the fiber sample density can be calculated.

A Duran glass volume standard was used to determine water density. This glass standard was certified to have a volume of 10+/−0.001 cubic centimeters (cc). During the experiment, the room temperature was recorded at 71° F. (22° C.). The glass standard was placed on a Mettler-Toledo AG204 series balance equipped with an integral immersion densitometer, previously tared to zero, and the mass was noted at 30.0409 g. A support was then placed over the balance base to allow a deionized water container to be placed over, but not in contact with, the balance. A support crucible was then suspended from the center of the balance into the water container and not allowed to contact the sides of the container. Any air bubbles attached to the crucible were removed by gentle agitation. The balance was then tared to zero. The glass standard was then carefully placed on the crucible and fully immersed in the water container, avoiding contact with the sides of the container. Any air bubbles attached to the glass standard after immersion in the water container were removed by gentle agitation of the glass standard on the crucible. The mass of the fully immersed glass standard was noted at 20.0465 g. The density of water was calculated as follows:

buoyancy mass for the 10 cc glass standard=30.0409 g−20.0465 g=9.9944 g water density=9.9944/10 cc=0.9994 g/cc.

All fibers with a density greater than 1 were tested using the following procedure. A fiber sample was placed on a Mettler-Toledo AG204 series balance equipped with an integral immersion densitometer, and the mass was noted in grams (A).

As described above in the density determination of water, a support was placed over the balance base to allow a water container to be placed over but not in contact with the balance. A support crucible was then suspended from the center of the balance into the water container and not allowed to contact the sides of the container. Any air bubbles attached to the crucible after immersion in the water container were removed by gentle agitation. The balance was then tared to zero. The fiber sample was then carefully placed on the crucible and fully immersed in the water container avoiding contact with the sides of the container. Any air bubbles attached to the fiber after immersion in the water container were removed by gentle agitation of the fiber on the crucible. The mass of the fully immersed fiber was noted in grams (B). The density of the fiber sample was calculated as follows:

fiber sample density (g/cc)=$A/((A-B)/0.9994)$.

For fiber densities less than 1, the fiber volume was calculated from the average thickness and width values of a fixed length of fiber and the density calculated from the fiber volume and mass of the fiber. For fibers with a density less than 1, a 1.8 meter length of fiber was placed on an A&D FR-300 balance and the mass noted in grams (C). The thickness of the fiber sample was then measured at 4 points along the fiber using a Heindenhain thickness gauge. The width of the fiber was also measured at 4 points along the fiber using a graduated eyepiece from Edmund Scientific Co. Average values of thickness and width were then calculated, and the volume of the fiber sample was determined (D). The density of the fiber sample was calculated as follows:

fiber sample density (g/cc)=$C/D$.

Dimensional Measurements

Thickness was measured between the two plates of a Mitutoyo/MAC micrometer, unless indicated otherwise. Three different sections were measured on each sample. The average of the three measurements was used.

Diameter was measured using a single beam laser measuring device (LaserMike optical micrometer Model Number 60-05-06). Five different sections were measured on each sample. The average of the five measurements was used.

Width was measured using a digital caliper. Three different sections were measured on each sample. The average of the three measurements was used.

Scraping Procedure

Scrapings of the islands of PTFE for DSC analysis were obtained in the following manner. A portion of the sample was wrapped around a glass slide and positioned such that the islands faced upwards, then the ends were taped to the slide to prevent the sample from moving. Only the islands were scraped from the sample using fresh razor blades, with the aid of magnification (20-30× under a stereoscope). To ensure that only island material was collected, it was visually confirmed that island material remained in each section from which scrapings were taken. This visual confirmation ensured that scrapings did not extend into the underlying node and fibril structure. Multiple samples were scraped to collect island material until approximately 1 mg of scrapings was so gathered for DSC analysis.

Fiber Fray Test Method Description

Fiber samples were tested using the fixture in FIG. 2 used for the Drag Resistance Test, described earlier, which provides the details of this fixture. Before each sample was tested, the cylinders were removed from the fixture, completely submerged in a beaker containing 99.9% isopropanol alcohol for 1 minute, replaced in the test fixture and permitted to air dry completely.

The test article was threaded around the three cylinders 170, 172 and 174 in the manner depicted in FIG. 2. Consequently, the sample was wrapped halfway around cylinder 170 and a quarter of the way around cylinders 172 and 174. Hence, a total cumulative wrap angle of one full wrap (i.e., $2\pi$ radians) was achieved. The sample did not have any twists between cylinders.

An INSTRON Model 5567 tensile tester outfitted with one yarn style clamping jaw was used. The gauge length was 50 mm (measured from the tangent point of the yarn clamp down to the tangent point of the test specimen resting against the first of the three cylinders 170). The fixture 180 was secured to the tensile tester such that the test specimen secured in the yarn style clamp was perpendicular to the axis of cylinder 170.

A 400 gram weight 186 was fixed to the end of the test specimen by tying a looped knot around a 400 gram weight. The length of the test specimen extending past cylinder 174 and down to the suspended 400 gram weight 186 was at least 150 mm. The tensile tester pulled the sample over the three cylinders a distance of 50.8 mm at a cross-head speed of 50.8 cm/min and then returned to its starting position to complete one cycle. Five consecutive cycles were run per sample.

The tested portion of the sample was marked by securing a piece of tape on the sample 12 mm past cylinder 170 toward the yarn style jaw and securing another piece of tape on the sample 63 mm past cylinder 172 toward cylinder 174.

The test method should be modified for fibers that do not have enough tensile strength to survive the test. If any of the desired number of samples break during the five cycles the weight should be lowered by 100 gram increments and the test should be started over until a weight is arrived at that does not cause any of the desired number of samples to break during the five cycles.

Upon completion of the test, the test samples were examined between the two pieces of tape for evidence of hairing. A hair is any part of the sample that has become frayed from the sample but is still attached at one end. Examination of the surface of the sample was performed using either a light ring with a 2× magnification lens or with a microscope (10× magnification). A caliper was used to measure the length of the hair, i.e., the length from the free end of the hair to the point where the hair is attached to the rest of the sample. The choice of magnification used, if any, is dependent on the ability to accurately detect and measure the length of the hairs.

The Fiber Fray Score for each sample was calculated from the length of the hairs coming off of the samples by the following equation:

Fiber Fray Score=sum of the lengths in millimeters of the hairs

Fishing Line Fray Test

The fishing line to be tested was cut to a length of about 7.62 meters. One end of the sample to be tested was tied using a fisherman's double Uni-knot to the free end of typical 12 lb test nylon fishing line that had been spooled onto a Shakespeare Tidewater 10LA bait casting reel (Shakespeare Fishing Tackle, Inc., Columbia, S.C.). The length of the nylon line was such that it filled ¼ of the spool on the reel. The reel was securely attached to the reel holder of a commercially available fishing pole (7 ft Gold Cup Inshore rod rated for 12-25 lb lines and ¾-3 oz. lures; Bass Pro Model GC171225, Springfield, Mo.). The pole was secured at approximately a 10-degree angle. The pole was secured 20 mm behind the last eyelet (toward the reel end of the pole) and 90 mm in front of the reel (toward the tip end of the pole). The tip was therefore allowed to move and vibrate by the tensions of the line and the inherent stiffness of the pole, as in a real fishing situation. The pole was secured in such a way that the line did not touch the securing devices during the test.

The other end of the sample fishing line to be tested was threaded through the pole guides and tied to a 16.83 cm diameter, about 50 mm wide, silicone coated take-up wheel in such a way that it did not slip or break during the test. The center of the wheel was located 15.24 cm beyond the pole tip (in the horizontal direction) and 34.3 cm below the pole tip (in the vertical direction). The 50 mm wide part of the wheel was positioned perpendicular to the fishing rod in such a way that the line could wind onto the 50 mm wide surface. This take-up wheel was attached to a DC motor that accelerated to 1750 rpm in approximately ¼ second. The rpm of the motor was measured with a digital hand tachometer (Ametek model 1726, Largo, Fla.) applied to the outside surface of the silicone take-up wheel.

The reel was set to the casting, or open, position. The motor was turned on and the line was wound onto the 50 mm wide part of the take-up wheel. This was intended to simulate casting the line during fishing. The motor was turned off after the entire sample had been wound onto the take-up wheel. Pressure was applied to the exposed metal side of the spool by hand with a piece of PFTE tape and a sponge to prevent the spool from over spinning while the take-up wheel was decelerating. The reel was switched to the closed or reeling position. An air drill (Matco Model MT1889, Stow, Ohio) attached to the handle of the reel in order to re-spool the line was turned on. The drill re-spooled the line at a rate of 85 to 88 feet per minute as measured by a digital hand tachometer (Ametek model 1726, Largo, Fla.) on the silicon surface of the wheel and with a back tension of 1800-2000 g applied to the wheel. The back tension was intended to simulate the resistance of a fish on the line and was measured by placing a Saxl Tension Meter Model TR-4000 (Tensitron, Inc., Harvard Mass.) onto the sample between the reel and the first eyelet as the sample was being reeled up by the air drill. A cycle was complete once the sample fishing line was respooled on the reel, minus the amount strung through the rod and tied onto the wheel. The air drill was turned off. Each line was subjected to 5 such test cycles.

Upon completion of the test, the test samples were examined over their entire length for evidence of hairs. A hair is any part of the line that has frayed and become separated from the line, but is still attached at one end. Examination of the surface of the sample was performed using either a light ring with a 2× magnification lens or with a microscope (10× magnification). A caliper was used to measure the length of the hair, i.e., the length from the free end of the hair to the point where the hair is attached to the rest of the sample. The choice of magnification used, if any, is dependent on the ability to accurately measure the length of the hairs.

A Fishing Line Fray Score for each sample was then calculated from the length of the hairs coming off of the samples using the following equation:

Fishing Line Fray Score=sum of the lengths in millimeters of hairs over 4 mm in length.

Moisture Vapor Transmission Rate (MVTR)

The samples (measuring larger than 6.5 cm in diameter) were conditioned in a 23° C., 50%+/−2% RH test room. Test cups were prepared by placing 70 grams of a Potassium Acetate salt slurry into a 4.5 ounce polypropylene cup having an inside diameter of 6.5 cm at the mouth. The slurry was comprised of 53 grams of potassium acetate crystals and 17 g of water. The slurry was thoroughly mixed with no undissolved solids present and stored for 16 hours in a sealed container at 23° C. An expanded PTFE membrane (ePTFE), available from W. L. Gore and Associates, Incorporated, Elkton, Md., was heat sealed to the lip of the cup to create a taut, leakproof microporous barrier holding the salt solution in the cup. A similar ePTFE membrane was mounted taut within a 12.7 cm embroidery hoop and floated upon the surface of a water bath in the test room. Both the water bath and the test room were temperature controlled at 23° C.

Samples to be measured were laid upon the floating membrane, and a salt cup inverted and placed upon each sample. The salt cups were allowed to pre-condition for 10 minutes. Each salt cup was then weighed, inverted and placed back upon the sample. After 15 minutes, each salt cup was removed, weighed, and the moisture vapor transmission rate was calculated from the weight pickup of the cup as follows:

$$MVTR\ g/(m^2 \times 24\ hours) = \frac{\text{Weight (g) water pickup in cup}}{[\text{Area (m}^2\text{) of cup mouth} \times \text{Time (days) of test]}}.$$

The average of five tests was used.

EXAMPLES

Figure 3:
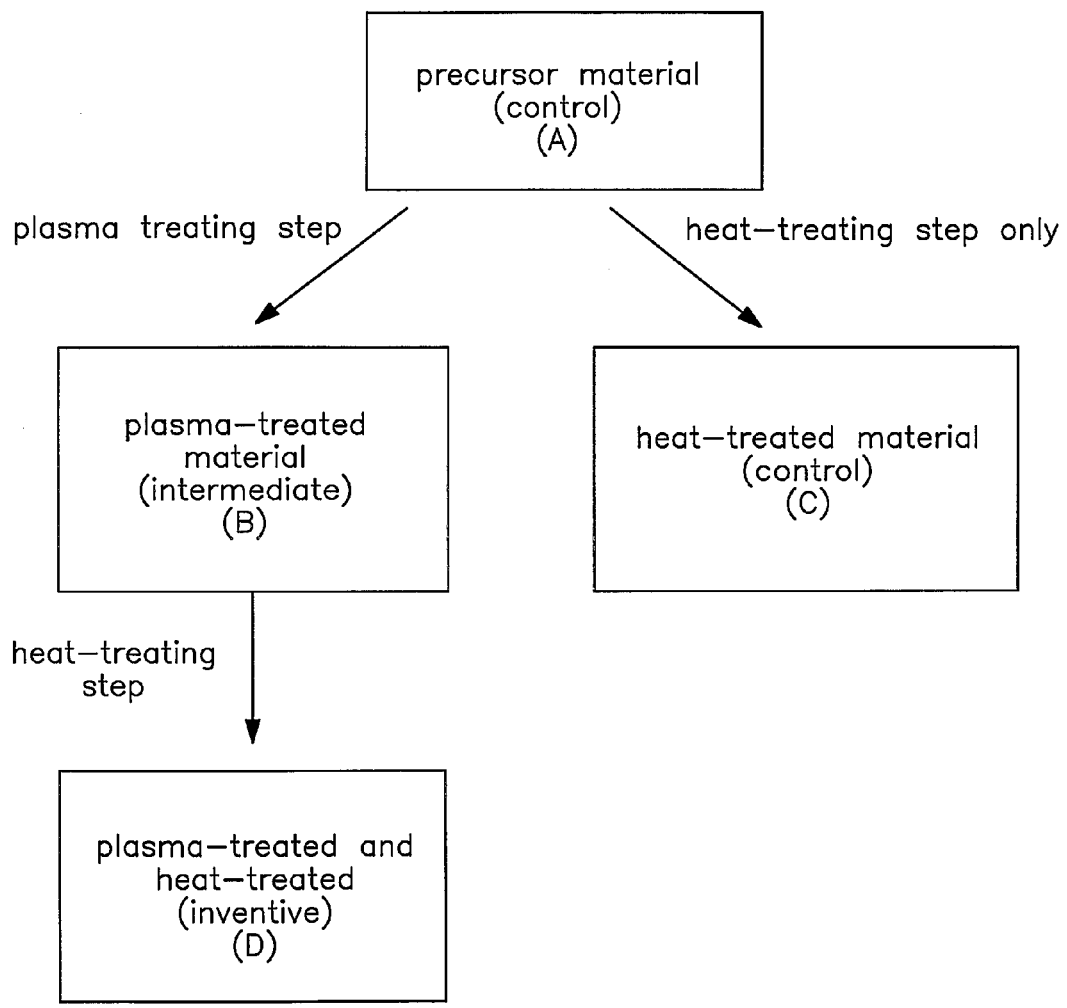
FIG. 3 is a schematic of the different comparative and inventive samples and treatments referred to in the Examples and Comparative Examples.

In order to demonstrate the unique surfaces of the materials of the present invention as compared to prior art surfaces and treatments, surface and longitudinal cross-section scanning electron micrographs were taken, in many cases, for each of the following three "comparative" materials and for the inventive material of the present invention: (A) precursor material; (B) plasma-treated only material, (C) heat-treated material only, and (D) inventive material that was subjected to the unique combination of plasma treating then heat treating to effect a unique surface on the inventive material. FIG. 3 is a schematic, for reference only, of the different comparative and inventive samples and treatments described in the following examples. Higher magnification images were taken in the same region that the low-magnification images were taken. Samples were thoroughly scanned to ensure that the images were representative of the sample.

Example 1

Precursor Material

Figure 4:
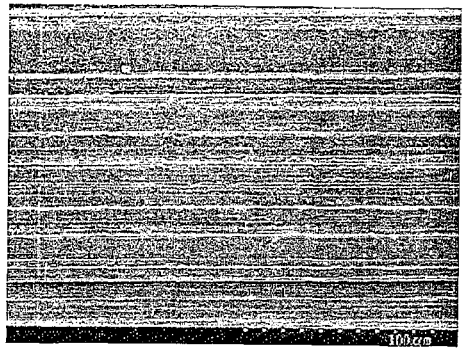
FIGS. 4-6 are photomicrographs of the prior art precursor material used in Example 1.
Figure 5:
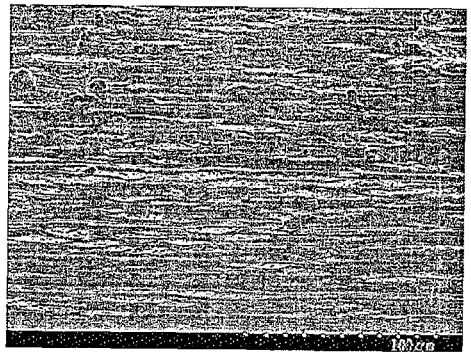
Figure 6:
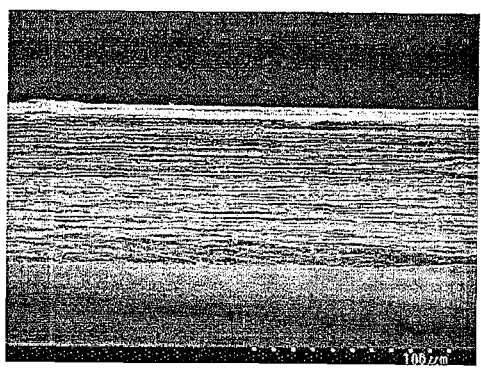

Expanded PTFE dental floss material made in accordance with the teachings of U.S. Pat. No. 5,518,012 was the precursor for the two continuous processing techniques performed in this example, described below as (a) and (b). This dental floss was an ePTFE flat fiber possessing the following properties: bulk density of 1.52 g/cc, thickness of 0.05 mm, width of 1.2 mm, and matrix tensile strength of 81,401 psi in the length direction, drag resistance of 0.148 and Fiber Fray Score of greater than 200 (exact numbers were not calculated because of the abundance of hairs). Representative scanning electron photomicrographs of the precursor material, all taken at 500× magnification, appear in FIGS. 4 through 6. The dashed bars present at the lower right of these and all other micrographs presented herein indicate the magnification scale. For example, the distance between the first and last dash marks in FIG. 4 corresponds to a length of 100 microns. The precursor material was produced by stretching PTFE over heated plates. FIGS. 4 and 5 show both of the surfaces of the precursor material, namely, the surface that did contact the plate and the surface that did not contact the plate, respectively. Islands of PTFE are not evident in either of these photomicrographs. FIG. 6, which shows a cross-section of the precursor material, also confirms the absence of islands in the precursor material. These three photomicrographs of the precursor material depict an ePTFE structure that is representative of highly longitudinally-expanded materials.

Experimental Procedures:

(a) Long lengths of the precursor material were first plasma treated using argon gas in conjunction with a Plasma Treatment System PT-2000P (Tri-star Technologies, El Segundo, Calif.). A T-section was affixed to the end of the nozzle of the unit. Plasma treatment occurred within the straight length of the T-section. The precursor floss material was fed through the straight section, which measured 59 cm long and 3.7 mm inner diameter. The floss material was drawn through the unit at a linear speed of 30 fpm, and the power was set between 2.1 and 2.2, per the "Plasma Current" display on the front of the unit. The argon flow rate was set at about 25 SCFH. The plasma-treated material was next subjected to a heat-treating step by passing it over a heated plate set to 390° C. at a line speed of 60 fpm. The length of the heated plate was 86 inches (2.2 m).

Figure 7:
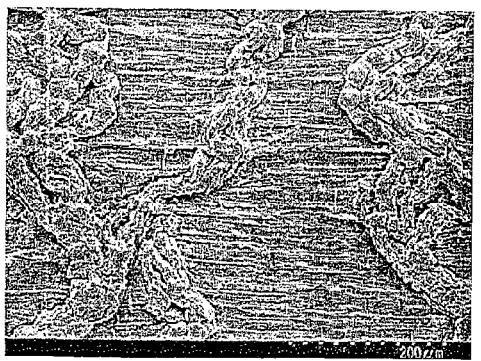
FIGS. 7-10 are photomicrographs of the inventive material made in accordance with Example 1.
Figure 8:
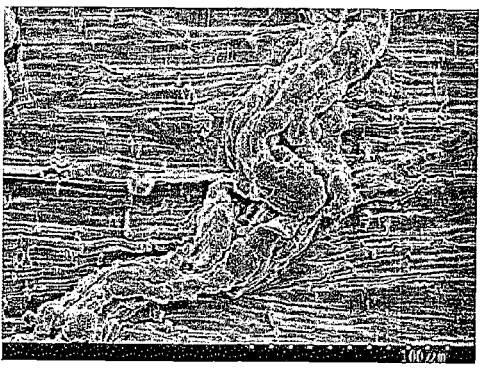
Figure 9:
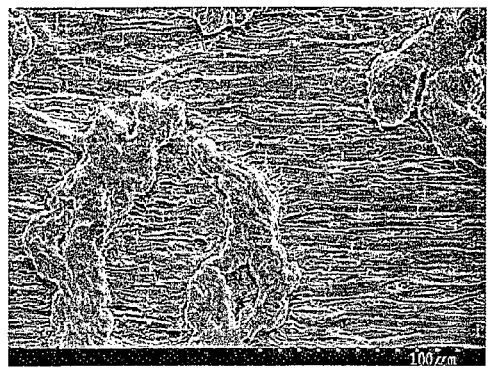
Figure 10:
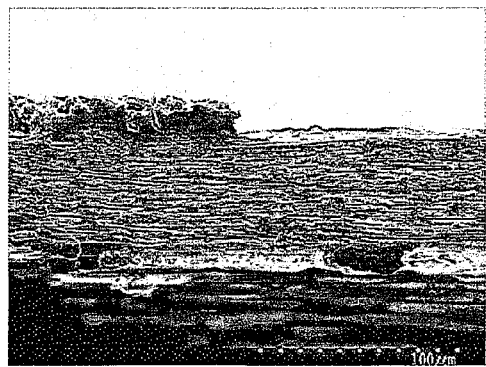

Photomicrographs of the plasma-treated, then heat-treated materials appear in FIGS. 7 through 10. FIG. 7 was taken at 200× magnification, and FIGS. 8 through 10 were taken at 500×. FIGS. 7 and 8 are surface shots taken of the plate side of the material, FIG. 9 is a surface shot taken of the non-plate side of the material, and FIG. 10 is a cross-sectional photomicrograph. The surface images indicate the smooth, island-like appearance of the PTFE material on top of the node-fibril structure of the underlying ePTFE floss material. These images demonstrate that the individual islands have a much larger surface area than any of the nodes of the underlying node-fibril ePTFE structure. The island height was determined to be about 17 microns.

The inventive article had the following properties: bulk density of 1.52 g/cc, longitudinal matrix tensile strength of 62,113 psi, width of 1.1 mm, and thickness of 0.05 mm. The inventive material had a drag resistance of 0.196, which was consistent with the perception of increased grippability and improved cleaning sensation experienced upon handling and using the inventive material. Three inventive samples were subjected to the Fiber Fray Test and were found to have no visible hairs, resulting in a Fiber Fray Score of 0.

(b) Another sample of the precursor material was processed in the same way as described above in procedure (a), except that faster line speeds of 200 feet per minute for both the plasma treating and subsequent heat treating were employed. The resulting inventive material had a drag coefficient of 0.192, and island height of 6 microns.

Comparative Example 1A

The same precursor material as described in Example 1, above, was used in this comparative example. A long length of the precursor material was plasma treated using argon gas in conjunction with a Plasma Treatment System PT-2000P (Tri-star Technologies, El Segundo, Calif.). A T-section was affixed to the end of the nozzle of the unit. Plasma treatment occurred within the straight length of the T-section. The precursor floss material was fed through the straight section, which measured 59 cm long and 3.7 mm inner diameter. The floss material was drawn through the unit at a linear speed of 30 fpm, and the power was set between 2.1 and 2.2, per the "Plasma Current" display on the front of the unit. The argon flow rate was set at about 25 SCFH.

Figure 11:
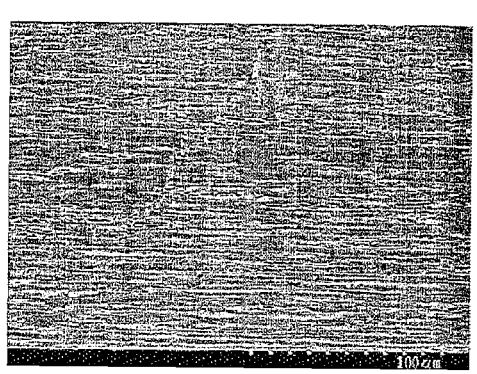
FIG. 11 is a photomicrograph of a prior art plasma-treated only material made in accordance with Comparative Example 1A.

This plasma treatment resulted in a material possessing the following properties: bulk density of 1.52 g/cc, thickness of 0.1 mm, width of 1.2 mm, and matrix tensile strength of 69,998 psi. FIG. 11 is a photomicrograph of this plasma-treated only material, showing a surface devoid of islands.

Comparative Example 1B

Figure 12:
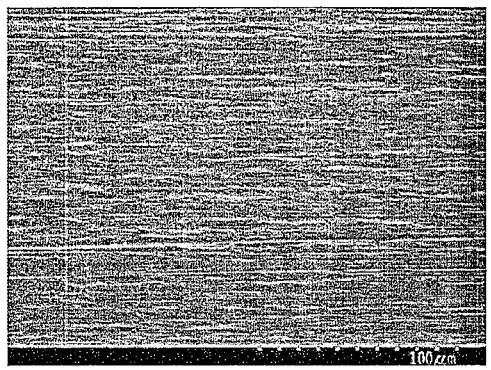
FIG. 12 is a photomicrograph of a prior art heat-treated only material made in accordance with Comparative Example 1B.

The same precursor material as described in Example 1, above, was used in this comparative example. A long length of the precursor material was subjected to a heat-treating step by passing it over a heated plate set to 390° C. at a line speed of 60 fpm. The length of the heated plate was 86 inches (2.2 m). FIG. 12 is a photomicrograph taken at 500× of the non-plate side of this heat-treated material. This image shows that the material surface is devoid of islands.

Example 2

The same precursor material as described in Example 1 was used in this example. The precursor material samples were subjected to the same plasma treatment described in Example 1, part (a), then the plasma-treated samples were axially restrained and placed in a forced air oven set to 335° C. for about 10 minutes.

Figure 13:
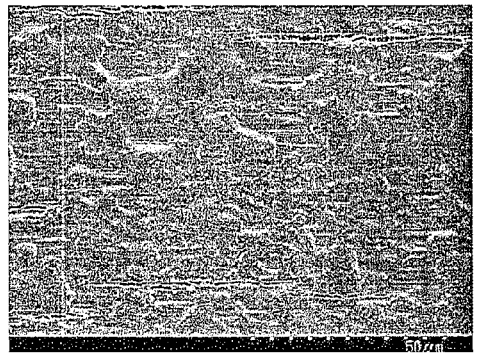
FIG. 13 is a photomicrograph of the inventive material made in accordance with Example 2.

Surface and longitudinal cross-section scanning electron photomicrographs were obtained for this inventive material. FIG. 13 is a surface photomicrograph of the floss material sample taken at 1000× magnification. The islands that are characteristic of articles of the present invention are evident in this photomicrograph. As with the islands observed in Example 1, the island surfaces appear smooth and the individual islands are of greater surface area than any of the underlying nodes.

The inventive article had the following properties: bulk density of 1.46 g/cc, longitudinal matrix tensile strength of 64,345 psi, width of 1.1 mm, and thickness of 0.17 mm. The inventive floss material, when tried by several individuals, gave the perception of improved grippability and cleaning sensation compared to the precursor material.

Example 3

Precursor Material

Figure 14:
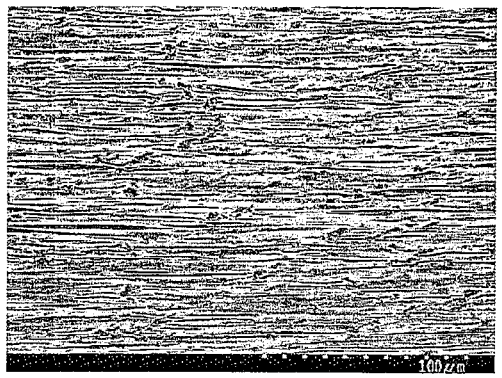
FIGS. 14 and 15 are photomicrographs of the precursor material used in Example 3.
Figure 15:
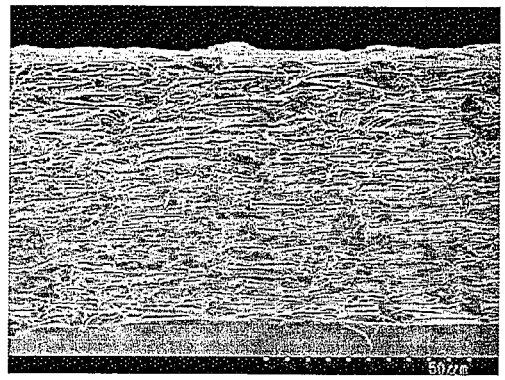

Expanded PTFE dental floss made in accordance with the teachings of U.S. Pat. No. 6,539,951 was the precursor material for this example. This dental floss consisted essentially of ePTFE and possessed the following properties: bulk density of 0.80 g/cc, thickness of 0.08 mm, width of 1.9 mm, matrix tensile strength of 63,949 psi, and drag coefficient of 0.172. Photomicrographs of the surface and cross-section, respectively, of this precursor material appear in FIGS. 14 (500×) and 15 (1000×).

Figure 16:
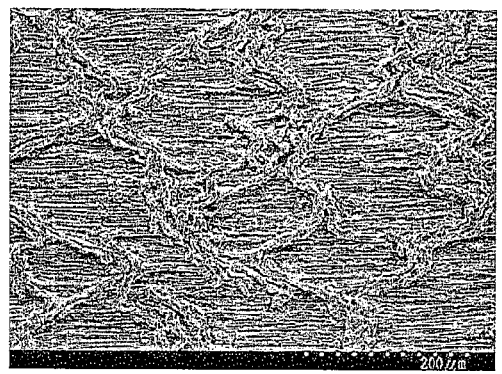
FIGS. 16-18 are photomicrographs of the inventive material made in accordance with Example 3.
Figure 17:
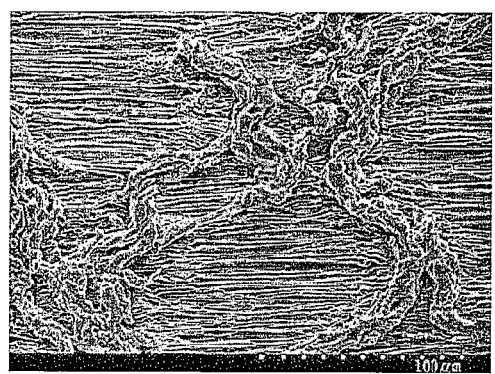
Figure 18:
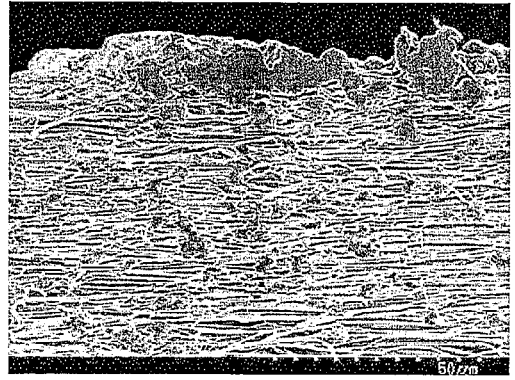

Experimental Procedure:

For the present example, the precursor material was plasma-treated, then heat treated in accordance with the steps described in Example 1, part (a). FIG. 16 (surface, 200×), FIG. 17 (surface, 500×), and FIG. 18 (cross-section, 1000×) are photomicrographs of the microstructure of the inventive material. As with the prior examples, the individual islands are seen to have a much larger surface area than any of the nodes of the underlying node-fibril ePTFE structure, and the islands exhibit a smooth surface. The inventive material had the following properties: bulk density of 0.82 g/cc, longitudinal matrix tensile strength of 36,707 psi, width of 1.8 mm, and thickness of 0.08 mm.

The average island height for the inventive material was determined to be about 13 microns. The drag coefficient for the inventive material was measured to be 0.220, thus indicating that the inventive article was more grippable than the precursor article and had an improved cleaning sensation.

Figure 19:
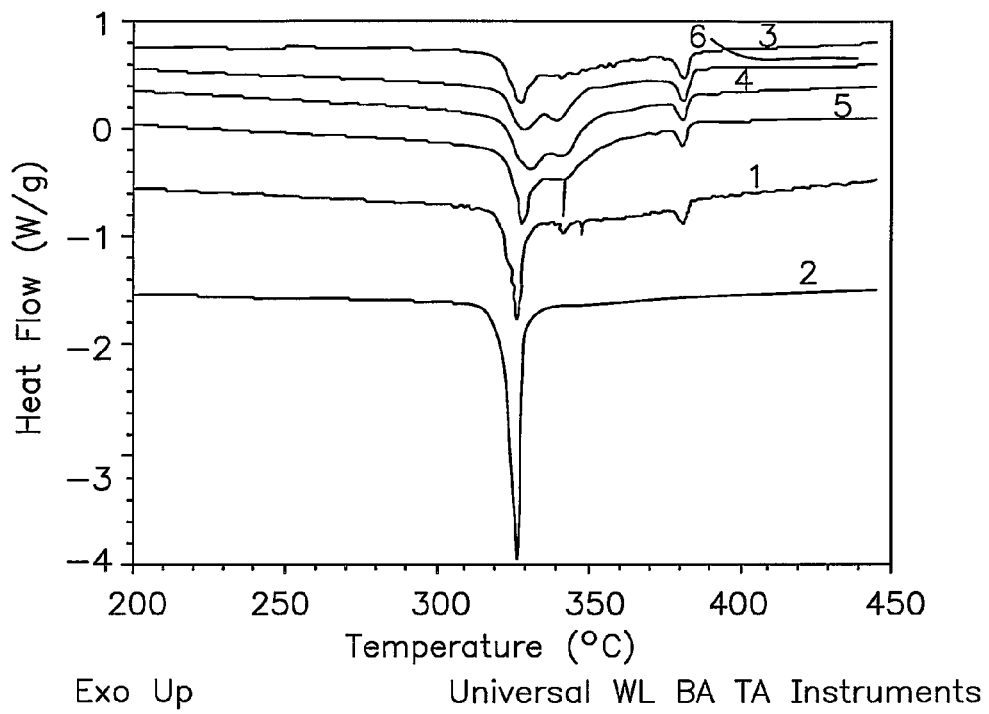
FIG. 19 is a graph showing the differential scanning calorimetry (DSC) scans comparing the features of the inventive materials with prior art materials, and described in more detail herein.

Differential Scanning Calorimetry (DSC) was used to determine whether multiple crystalline phases of PTFE existed in the islands and in the underlying core, or non-island, component of the material made in this example. Scrapings of the islands were taken by following the Scraping Procedure described herein. FIG. 19 herein includes the DSC scans for the inventive material as a whole, as well as for the scrapings alone and the underlying core alone. The results are described in more detail later herein, along with comparisons with Comparative Example 3A and 3B material scans.

Comparative Example 3A

The precursor material described in Example 3 was used for this comparative example. This precursor material was subject to the same plasma treatment described in Comparative Example 1A.

Comparative Example 3B

The precursor material described in Example 3 was used for this comparative example. This precursor material was subject to the same heat treatment described in Comparative Example 1B.

FIG. 19 shows six DSC heating scans for the inventive materials of Example 3 (labeled (1), (2) and (3) on the figure), the precursor material for Example 3 (labeled (4)), and for Comparative Example 3A (labeled (5)) and 3B (labeled (6)). All samples were tested in the manner described in the Test Method for Determination of Crystalline Phases in Polytetrafluoroethylene Material based on Differential Scanning Calorimetry. The curves were overlaid on the same graph and shifted on the y-axis for clarity. The curve corresponding to the inventive sample is labeled as (1). Islands from a section of this sample were scraped off the surface per the Scraping Procedure, and the heating scan for this island material is labeled (2). A scan was also prepared by obtaining core material from the center of the inventive material sample, ensuring that all island material was removed, and the curve for this core material is labeled (3).

All but one of the scans in this FIG. 19 exhibit the approximately 380° C. peak in the heating curves. The only sample that did not exhibit this peak was the island material obtained by scraping (scan (2)). The absence of this endotherm in this DSC curve indicates that the islands do not contain the node and fibril structure that is present in all of the other materials. This result is consistent with the absence of discernable fibrils in the islands evidenced in the micrographs.

From the DSC cooling scan, the exothermic enthalpy (as expressed in units of J/g) represented by the area of the peak at approximately 316° C. provides information regarding the molecular weight of the PTFE. Lower molecular weight PTFE has higher enthalpic values because the material can recrystallize more readily during cooling than higher molecular weight PTFE. The exothermic enthalpy of the core of the inventive material devoid of all islands, represented by the area of the peak at approximately 316° degree C., was 33.5 J/g. The exothermic enthalpy of the island scrapings had an exothermic enthalpy, represented by the area of the peak at approximately 316° C., of 60.5 J/g. The higher exothermic enthalpy of the islands as compared to the core indicated that the islands were comprised of lower molecular weight PTFE than the core.

Example 4

Figure 20:
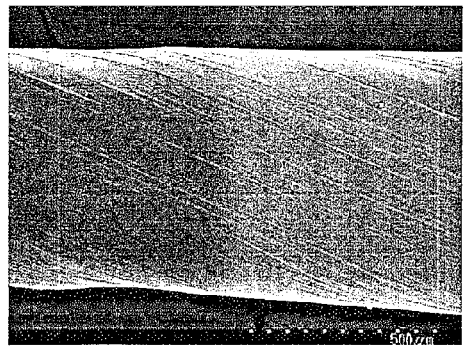
FIG. 20 is a photomicrograph of the precursor material used in Example 4.

Expanded PTFE fiber was obtained (Part Number V12765, available from W. L. Gore and Associates, Inc., Elkton, Md.), and two such fibers were twisted together to provide the precursor material for this example. The precursor material possessed the following properties: bulk density of 1.29 g/cc, longitudinal matrix tensile strength of 138,278 psi, and diameter of 0.483 mm. FIG. 20 (100×) is a photomicrograph of the surface of the precursor material.

In this example, the precursor material was plasma treated and heat treated in the same manner as described in Example 1, part (a), except that the plasma treatment line speed was set at 100 fpm, and the heat treatment was performed over a series of three heated plates, measuring 9 feet total, all set to 440° C. to effect a modest amount of shrinkage by applying an overall stretch ratio of 0.92:1.

Figure 21:
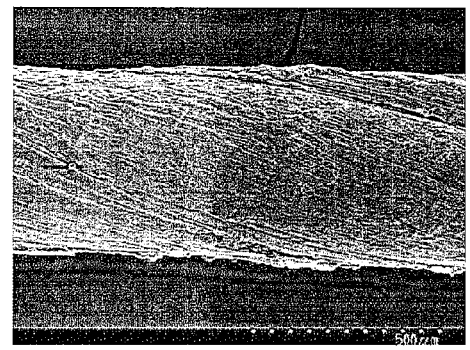
FIGS. 21 and 22 are photomicrographs of the inventive material made in accordance with Example 4.
Figure 22:
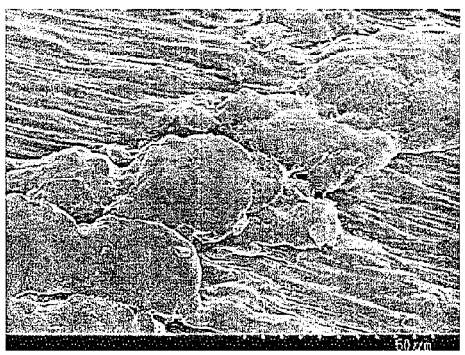

The inventive article had the following properties: bulk density of 2.17 g/cc, longitudinal matrix tensile strength of 92,285 psi, diameter of approximately 0.41 mm. The cross-section of the article was of oblong shape. The island height was determined to be about 6 microns. FIG. 21 (100×) and FIG. 22 (1000×) are surface photomicrographs of the inventive material. Both figures show raised, smooth-surfaced islands.

In addition, three samples of the inventive fishing line material were subjected to the Fishing Line Fray Test, and all of the inventive fishing lines exhibited only small hairs ranging from 0.5 mm to 6 mm in length. Fishing Line Fray Scores for these three samples were 4, 5, and 10, respectively.

Comparative Example 4A

The precursor material described in Example 4 was used for this comparative example. Comparative fishing line material were made by heat treating the precursor over a series of three heated plates, all set to 440° C. to effect a modest amount of shrinkage by applying an overall stretch ratio of 0.92:1.

Three comparative fishing line samples were subjected to the Fishing Line Fray Test. Each of the three samples had many hairs of varying lengths from 0.5 mm to as long as 38 mm, with at least 10 hairs over 10 mm in length and at least two hairs over 20 mm in length. The Fishing Line Fray Scores for these samples were all over 160 (exact numbers were not obtained because of the abundance of hairs).

Example 5

Figure 23:
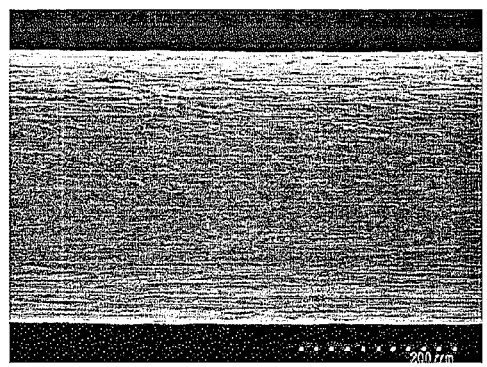
FIG. 23 is a photomicrograph of the precursor material used in Example 5.

The precursor material for this example was expanded PTFE suture material possessing the following properties: bulk density of 1.13 g/cc, longitudinal matrix tensile strength of 56,382 psi, and diameter of 0.3 mm. FIG. 23 is a photomicrograph taken at 200× of the precursor material.

Figure 24:
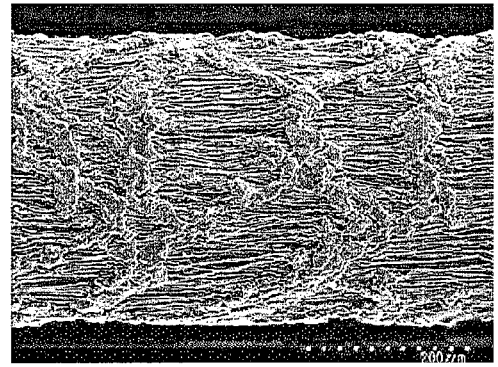
FIG. 24 is a photomicrograph of the inventive material made in accordance with Example 5.

This precursor material was plasma treated in the same manner as described in Example 1 (a); however, the subsequent heat treating was performed in a continuous manner, drawing the plasma treated article through a 92-inch-long forced air oven set to 415° C. at a line speed of about 15 ft/minute. The resulting inventive article had the following properties: bulk density of 1.07 g/cc, longitudinal matrix tensile strength of 44,986 psi, and a diameter of 0.33 mm. The island height was determined to be about 11 microns. FIG. 24 is a photomicrograph taken at 200× of the inventive material.

FIGS. 23 and 24 demonstrate the difference in the surface appearance between the precursor and inventive materials, respectively. The inventive material clearly exhibits the raised islands of PTFE, in which the islands are smooth and are of greater size than the nodes of the underlying structure. As with all of the images included herein, samples were thoroughly scanned to ensure that the images were representative of the sample.

The inventive materials were subjected to the Knot Holding Capacity Test, and the knotted inventive article retained 59% of its material peak force, and the inventive suture broke at the knot in 70% of the cases.

For comparison purposes, a sample of the knotted precursor suture material, when subjected to the Knot Holding Capacity Test, retained only 27% of its material peak force and in each test the knot slipped without the suture breaking.

Example 6

Figure 25:
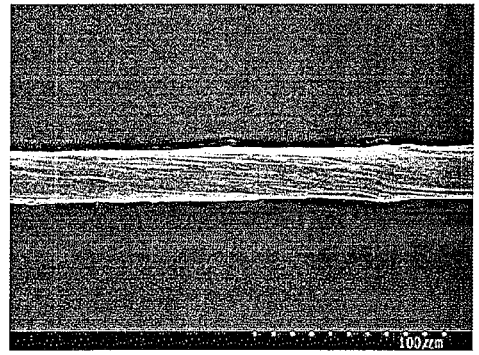
FIG. 25 is a photomicrograph of the precursor material used in Example 6.

The precursor material for this example was an expanded PTFE fiber material, suitable for use as a suture, having a diameter of 0.023 mm. FIG. 25 is a photomicrograph taken at 500× of the precursor material.

Figure 26:
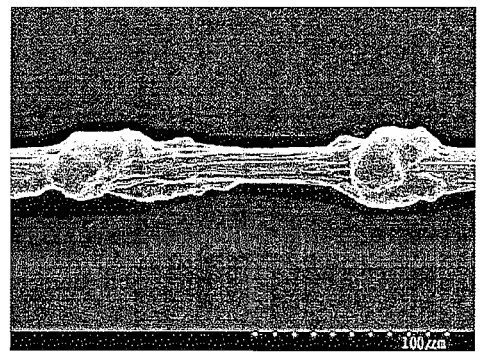
FIG. 26 is a photomicrograph of the inventive material made in accordance with Example 6.

The precursor material was first plasma treated using argon gas in conjunction with a Plasma Treatment System PT-2000P (Tri-star Technologies, El Segundo, Calif.). A T-section was affixed to the end of the nozzle of the unit. Plasma treatment occurred within the straight length of the T-section. The precursor floss material was fed through the straight section, which measured 59 cm long and 3.7 mm inner diameter. The floss material was drawn through the unit at a linear speed of 5 fpm, and the power was set at 1.8, per the "Plasma Current" display on the front of the unit. The argon flow rate was set at about 25 SCFH. The plasma-treated material was next restrained from shrinking by tying it to a metal frame, then subjected to a heat-treating step by placing it in a forced air oven set to 335° C. for 10 minutes. Islands of PTFE are evident on the inventive material, as shown in FIG. 26, which is a photomicrograph taken at 500×.

Example 7

Figure 27:
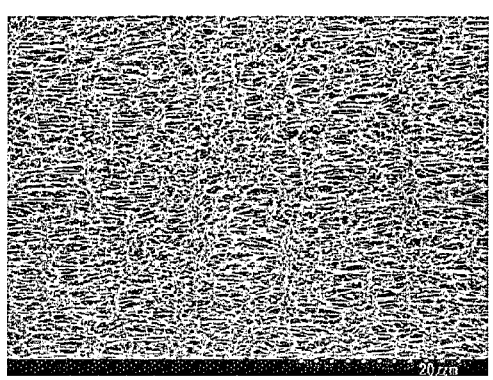
FIGS. 27 and 28 are photomicrographs of the precursor material used in Example 7.
Figure 28:
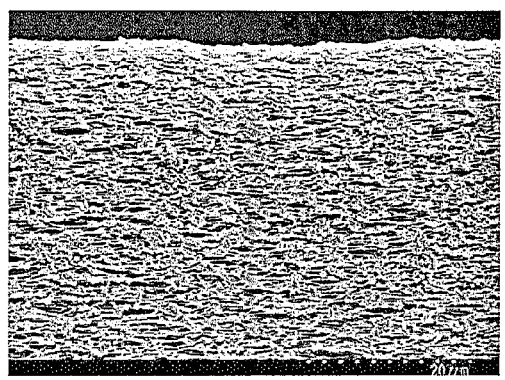

The precursor material for this example was an expanded PTFE membrane possessing the following properties: moisture vapor transmission rate of 68,149 g/m$^2$-day, thickness of 0.023 mm, bulk density of 0.80 g/cc, longitudinal matrix tensile strength of 8,740 psi, and transverse matrix tensile strength of 15,742 psi. FIGS. 27 and 28 are photomicrographs of the surface and the cross-section, respectively, of the precursor membrane, both taken at 2000× magnification.

The membrane material was then processed to provide articles of the present invention. The precursor membrane was subjected to a plasma treatment using argon gas by passing the membrane through an atmospheric plasma treatment unit set to a power of 2.5 kilowatts. The membrane was passed through the unit at a speed of 5 meters per minute, and the argon gas flow rate was 50 liters per minute. The plasma-treated membrane was subsequently restrained from shrinking by securing it on a pin frame and heat treated in a forced air oven set to 335° C. for about 10 minutes.

Figure 29:
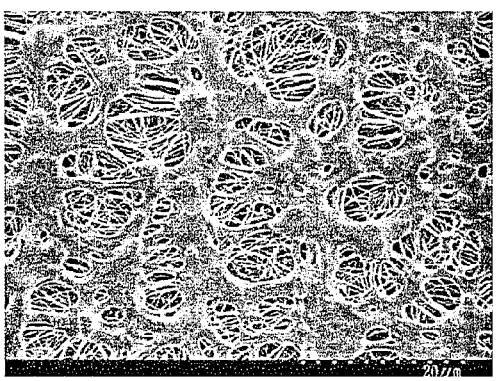
FIGS. 29 and 30 are photomicrographs of the inventive material made in accordance with Example 7.
Figure 30:
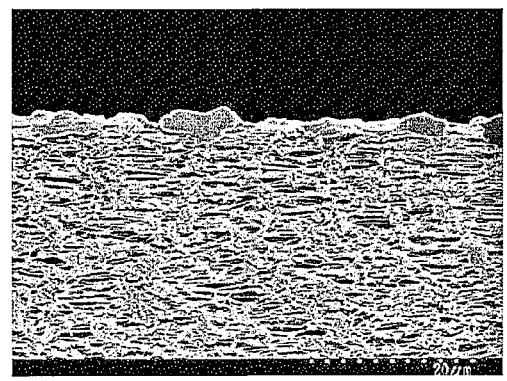

The resulting inventive material had the following properties: bulk density of 0.81 g/cc, longitudinal matrix tensile strength of 10,070 psi, transverse matrix tensile strength of 14,375 psi, and thickness of 0.023 mm. FIGS. 29 and 30 are surface and cross-sectional photomicrographs, respectively, of the inventive material taken at 2000×, showing smooth, raised islands. The island height of the inventive material was determined to be about 3 microns.

Example 8

The same precursor membrane material described in Example 7 was used for this example. The precursor was processed in the same manner described in Example 7, except that round silica particles (Admatechs, Product Number SO-E2, Seto, Japan) were applied to the surface of the plasma-treated membrane by sprinkling, then the particles were spread out by a gloved hand to form a thin, substantially even coating on the membrane prior to the heat-treating step.

A photomicrograph of the surface of the inventive article taken at 2000× appears in FIG. 31. Upon examination of the photomicrograph, it was observed that the raised islands contained silica particles.

Example 9

The precursor membrane material described in Example 7 was used for this example. The membrane was processed in the same manner as described in Example 7, except that a mask material comprising a polyester film tape with a rubber adhesive (3M™ Polyester Protective Tape 335, Minnesota Mining and Manufacturing, Inc., St. Paul, Minn.) having a pattern of substantially regularly-spaced holes was taped to the surface of the precursor material prior to the plasma-treatment step. The mask was removed after the plasma-treatment, but prior to the heat treatment step.

FIGS. 32 and 33 are surface shots taken at 70× and 2000×, respectively, of the resulting article of this example. FIG. 32 shows the dot pattern effected by masking the PTFE during the plasma-treating process. Specifically, the areas that appear as dots (darker) 501 are areas that were plasma-treated then heat-treated; hence, these regions were processed in accordance with the present invention. The masked (lighter) regions 502 were subjected only to heat treatment. A representative higher magnification image of the boundary between the masked 502 and unmasked 501 regions is presented in FIG. 33. Note the smooth islands 503 on the plasma-treated and heat-treated area, as compared to the masked region 502.

Example 10

A precursor material comprising expanded PTFE fiber which had never been subjected to amorphous locking temperatures was obtained having the following properties: bulk density of 1.2 g/cc, longitudinal matrix tensile strength of 71,000 psi, width of 1.2 mm, and thickness of 0.2 mm.

The precursor material was processed in the same manner as part (a) of Example 1. The resulting inventive article had the following properties: bulk density of 1.4 g/cc, longitudinal matrix tensile strength of 64,400 psi, width of 0.9 mm, and thickness of 0.2 mm. A photomicrograph taken at 500× of the surface of the resulting inventive material appears in FIG. 34. This figure shows the raised islands of PTFE on the material, thus demonstrating that articles of the present invention are created even with ePTFE precursor materials which have not been subjected to amorphous locking temperatures.

While the invention has been disclosed herein, in connection with certain embodiments and detailed descriptions, it will be clear to one skilled in the art that modifications or variations of such detail can be made without deviating from the gist of the invention and such modifications or variations are considered to be within the scope of the claims herein below.

We claim:

1. An article comprising:
   a first, expanded PTFE material having an outer surface which defines a baseline, and
   raised islands comprising PTFE originating from the first, expanded PTFE material and extending above the baseline.

2. The article of claim 1, wherein said raised islands are of lower molecular weight than the PTFE of the underlying PTFE material from which they extend.

3. The article of claim 1 in the form of a fiber.

4. The article of claim 1 in the form of a membrane.

5. The article of claim 1, further comprising at least one filler material.

6. The article of claim 5, wherein the at least one filler is in the expanded PTFE material.

7. The article of claim 5, wherein the at least one filler is in the raised islands.

8. The article of claim 1, wherein said raised islands are oriented on the underlying PTFE material in a patterned configuration.

9. The article of claim 1, wherein said islands do not exhibit a melt temperature upon differential scanning calorimetry at or above 380° C.

10. The article of claim 1 in the form of a sheet.

11. The article of claim 1 in the form of a tube.

12. The article of claim 1, wherein said article is in the form of a plurality of monofilament fibers combined in a twisted configuration.

13. An article comprising:
    a plurality of monofilament fluoropolymer fibers combined in a twisted configuration,
    said twisted configuration having a density >1 g/cc and a fiber fray scored <100.

* * * * *

UNITED STATES PATENT AND TRADEMARK OFFICE
CERTIFICATE OF CORRECTION

| | | |
|---|---|---|
| PATENT NO. | : 7,615,282 B2 | Page 1 of 1 |
| APPLICATION NO. | : 12/263881 | |
| DATED | : November 10, 2009 | |
| INVENTOR(S) | : Lutz et al. | |

It is certified that error appears in the above-identified patent and that said Letters Patent is hereby corrected as shown below:

Column 1, line 51 change "6,573.311" to --6,573,311--.

Column 1, line 36 change "4,2308,745" to --4,208,745--.

Column 5, line 38 change "(Ra." to --(Ra)--.

Column 6, line 50 change "in is" to --In is--.

Column 7, line 50 change "was by performed" to --was performed--.

Column 16, line 4 change "Jig" to --J/g--.

Column 16, line 60 change "V12765" to --V112765--.

Signed and Sealed this

Twenty-second Day of June, 2010

David J. Kappos
*Director of the United States Patent and Trademark Office*